(12) United States Patent
Pitta' et al.

(10) Patent No.: US 11,442,031 B2
(45) Date of Patent: Sep. 13, 2022

(54) APPARATUS FOR SELECTING PRODUCTS ON THE BASIS OF THEIR COMPOSITION BY X RAY FLUORESCENT SPECTROSCOPY AND CORRESPONDING SELECTION METHOD

(71) Applicants: DE.TEC.TOR. S.r.l., Turin (IT); ACCIAIERIE VALBRUNA S.p.A., Vicenza (IT)

(72) Inventors: Giuseppe Pitta', Turin (IT); Massimo Amenduni, Vicenza (IT); Mauro Zona, Turin (IT)

(73) Assignees: DE.TEC.TOR S.r.L., Turin (IT); ACCIAIERIE VALBRUNA S.p.A., Vicenza (IT)

( * ) Notice: Subject to any disclaimer, the term of this patent is extended or adjusted under 35 U.S.C. 154(b) by 0 days.

(21) Appl. No.: 16/643,996

(22) PCT Filed: Aug. 30, 2018

(86) PCT No.: PCT/IB2018/056637
§ 371 (c)(1),
(2) Date: Mar. 3, 2020

(87) PCT Pub. No.: WO2019/049000
PCT Pub. Date: Mar. 14, 2019

(65) Prior Publication Data
US 2021/0063328 A1   Mar. 4, 2021

(30) Foreign Application Priority Data
Sep. 6, 2017 (IT) .................. 102017000100060

(51) Int. Cl.
*G01N 23/223* (2006.01)
*G01N 33/202* (2019.01)
(Continued)

(52) U.S. Cl.
CPC ............ *G01N 23/223* (2013.01); *G01B 9/02* (2013.01); *G01B 11/0608* (2013.01);
(Continued)

(58) Field of Classification Search
CPC .... G01N 23/00; G01N 23/223; G01N 33/202; G01N 2223/624; G01N 2223/076;
(Continued)

(56) References Cited

U.S. PATENT DOCUMENTS 8,475,042 B1   7/2013   Reilly
9,031,187 B2   5/2015   Yellepeddi et al.
(Continued)

OTHER PUBLICATIONS

International Search Report and Written Opinion of the ISA for PCT/IB2018/056637, dated Jan. 3, 2019, 12 pages.

*Primary Examiner* — Jurie Yun
(74) *Attorney, Agent, or Firm* — Nixon & Vanderhye P.C.

(57) ABSTRACT

An apparatus for selecting products on the basis of their composition via X-ray fluorescence spectroscopy includes an X-ray source that emits an X-ray beam towards a product sample, and a particle detector for receiving an X-ray beam diffused by the product sample and generating a signal received that can be analysed to determine a chemical composition of the product sample and selecting a type of product corresponding to said chemical composition of the product sample. The apparatus includes a first vacuum chamber located between an output of the apparatus facing the product sample and the X-ray source, and a second vacuum chamber located between the output of the apparatus facing the product sample and the detector. The apparatus also includes an optical module with polycapillary lens located downstream of the X-ray source, which is configured for focusing the X-ray beam and is associated in a vacuum-tight way to the first vacuum chamber.

13 Claims, 6 Drawing Sheets

(51) Int. Cl.
    *G01B 9/02*         (2022.01)
    *G01B 11/06*      (2006.01)

(52) U.S. Cl.
    CPC ..... *G01N 33/202* (2019.01); *G01N 2223/076* (2013.01); *G01N 2223/3308* (2013.01); *G01N 2223/507* (2013.01); *G01N 2223/624* (2013.01); *G01N 2223/643* (2013.01)

(58) Field of Classification Search
    CPC ..... G01N 2223/507; G01N 2223/3308; G01N 2223/643; G01B 11/06; G01B 11/0608; G01B 9/02
    See application file for complete search history.

(56) References Cited

U.S. PATENT DOCUMENTS

| | | |
|---|---|---|
| 2003/0147494 A1 | 8/2003 | Sommer, Jr. et al. |
| 2011/0007869 A1 | 1/2011 | Gendreau et al. |
| 2017/0014868 A1 | 1/2017 | Garcia, Jr. et al. |

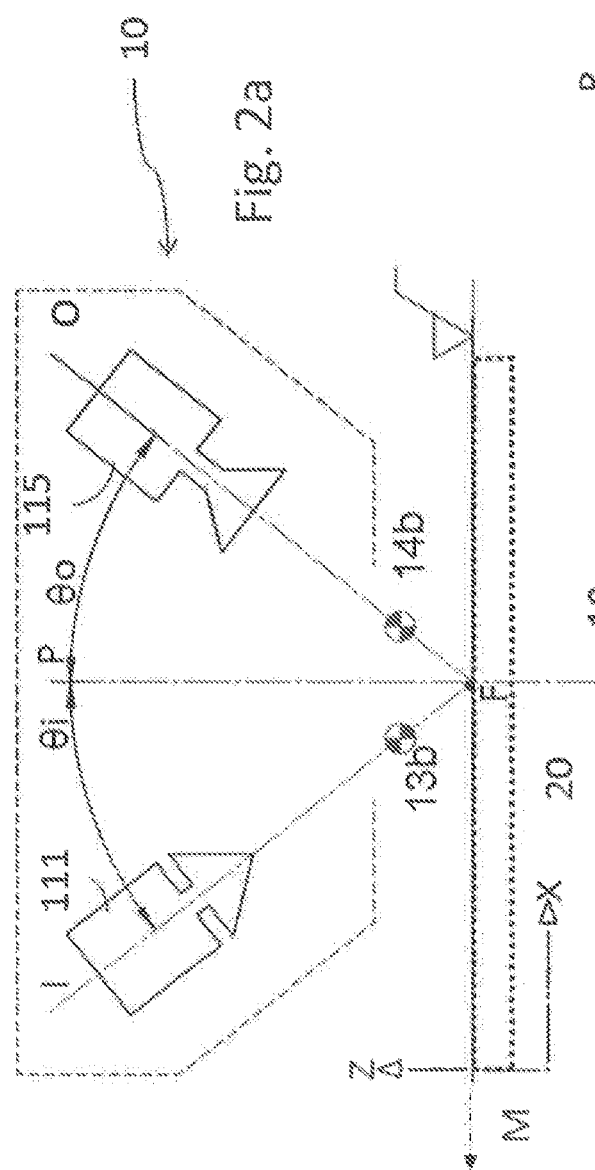
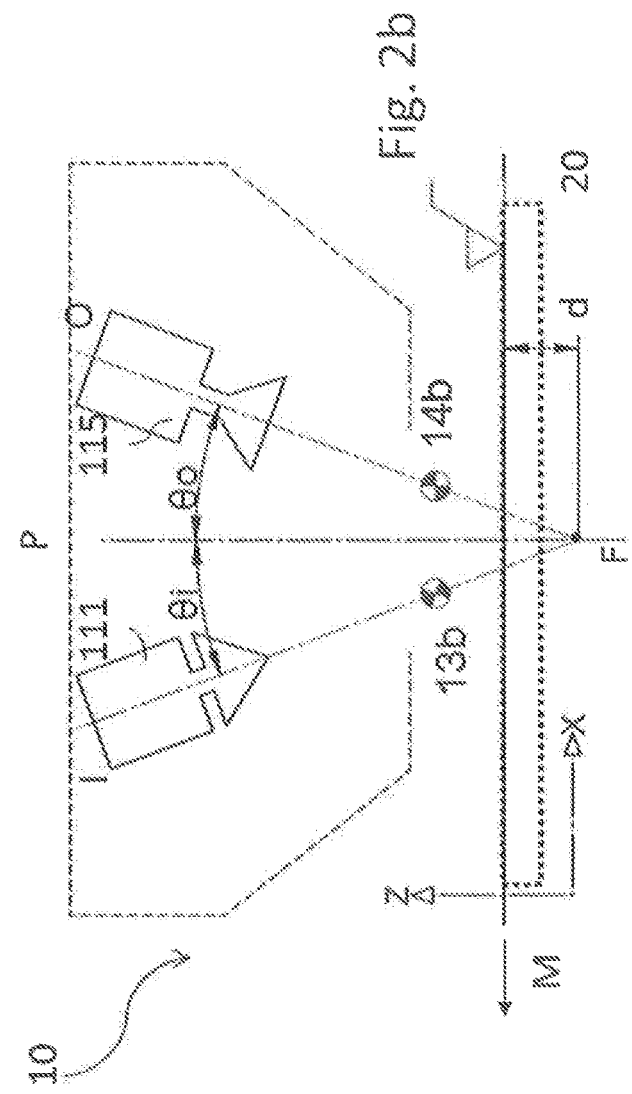

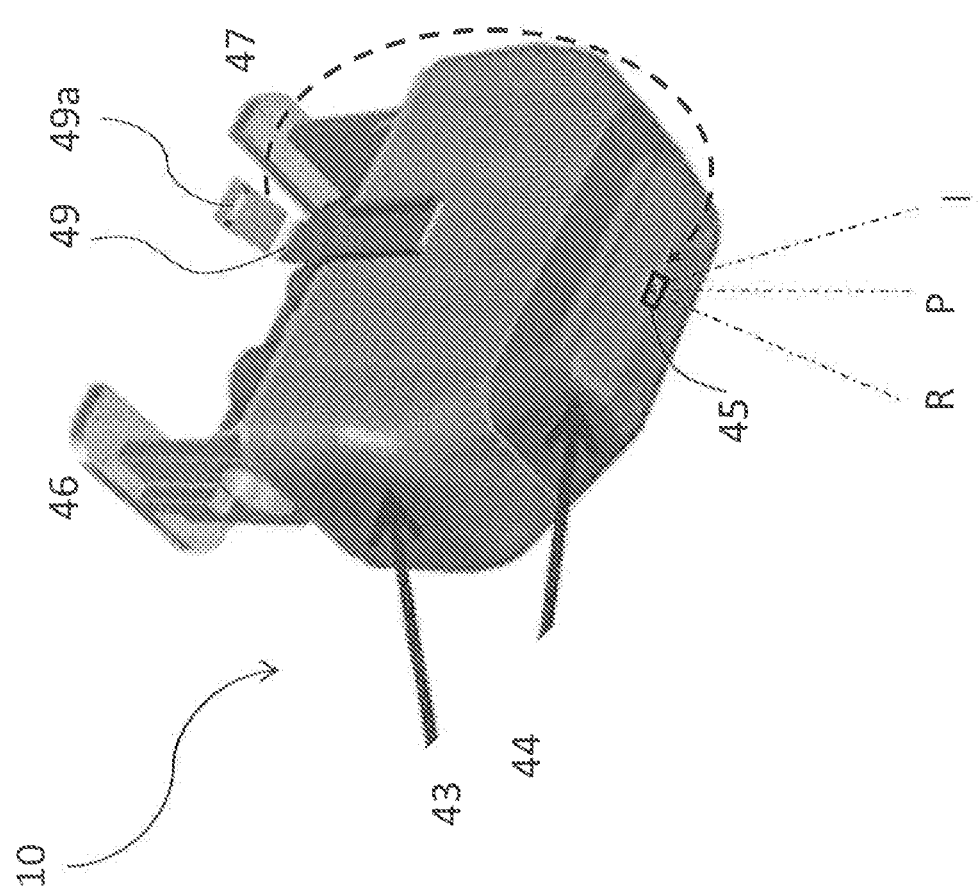

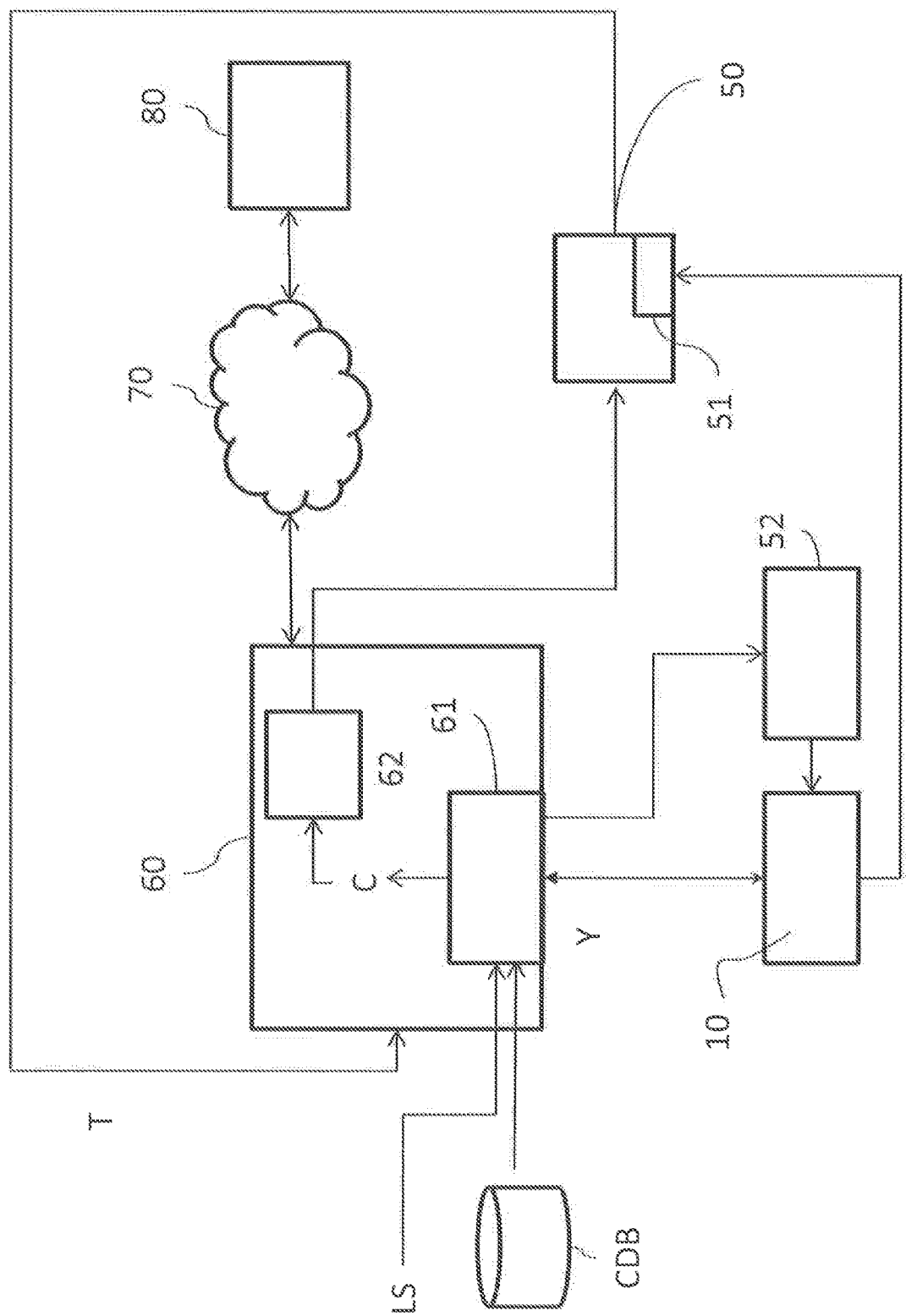

APPARATUS FOR SELECTING PRODUCTS ON THE BASIS OF THEIR COMPOSITION BY X RAY FLUORESCENT SPECTROSCOPY AND CORRESPONDING SELECTION METHOD

This application is the U.S. national phase of International Application No. PCT/IB2018/056637 filed 30 Aug. 2018, which designated the U.S. and claims priority to IT Patent Application No. 102017000100060 filed 6 Sep. 2017, the entire contents of each of which are hereby incorporated by reference.

TECHNICAL FIELD

The present disclosure relates to techniques for selecting products on the basis of their composition via X-ray fluorescence spectroscopy.

In particular, the present invention relates to techniques for selecting and preventing mixing of metal-matrix products, in particular in processes of production of the aforesaid products.

TECHNOLOGICAL BACKGROUND

In the production flow of metal-matrix products, such as production of steel alloys, three main production steps are identified: smelting in the steelworks, hot processing, and cold processing.

It is hence necessary to proceed to identification and tracing of the products in their different production steps in order to guarantee that each single type of product, identified, for example, by a composition of the product, the so-called product mark or name, will follow the production path envisaged for its purpose of use.

It is known to use for this purpose methods of quality control that envisage carrying out chemical analyses on samples, amongst which with the use of XRF (X-Ray Fluorescence) spectroscopy instrumentation of a contact portable type.

The XRF spectroscopy technique is a non-destructive technique of analysis that makes it possible to discover the elementary composition of a sample through the study of X-ray fluorescence. X rays are emitted by the atoms of the sample following upon excitation, which is typically obtained by irradiating the sample in contact with high-energy X-rays and gamma rays.

The aforesaid XRF technique is used in the industrial field for carrying out chemical analysis of a product, on account of a series of advantages that this technique affords, such as high precision and repeatability of the method, the fact that complex calibration procedures are not required, the short times of analysis, and the wide analytical range that can be determined.

XRF spectrophotometry analyses are usually carried out with a static sample, i.e., one that is not moving, set in contact with the analyser and at room temperature. Moreover, the sample is pre-treated for carrying out the measurement.

However, in order to select and avoid any mixing of the products being processed within a production cycle, it is problematical to carry out an XRF analysis on line, where the sample or product, for example a steel bar, may present in the following conditions:

in the presence of different levels of contamination, such as surface oil and oxides;
moving at a rate that may range between 5 and 80 m/min;
at temperatures higher than room temperature, up to, for example, 1200° C.

This would hence require carrying out the analysis not only with the bar stationary, but also with the bar in axial movement, in different temperature conditions (hot product, such as at output from an oven or along a rolling line) in such a way as to monitor and compare the product chemical analyses in the various processing steps with the chemical analyses made during casting.

Consequently, known solutions, which amount to sample tests on material in stationary conditions along the production line at room temperature and in contact with the analyser, present limits that do not allow chemical analysis to be conducted in a continuous production flow.

OBJECT AND SUMMARY

The object of the embodiments described herein is to improve the apparatuses and processes according to the prior art, as discussed previously.

Various embodiments achieve the above object thanks to an apparatus having the characteristics recalled in the ensuing claims.

The claims form an integral part of the technical teachings provided herein in relation to the invention.

In particular, the solution described herein regards an apparatus for selecting products on the basis of their composition via X-ray fluorescence spectroscopy, which comprises an X-ray source that emits an X-ray beam towards a product sample, and a particle detector for receiving an X-ray beam diffused by said product sample and generating a signal received that can be analysed to determine a chemical composition of said product sample and select a type of product corresponding to said chemical composition of the product sample, where the apparatus comprises: a first vacuum chamber located between an output of the apparatus facing the product sample and said X-ray source; and a second vacuum chamber located between said output of the apparatus facing the product sample and said detector.

In variant embodiments, the above apparatus for selecting products on the basis of their composition via X-ray fluorescence spectroscopy further comprises an optical module with polycapillary lens located downstream of said X-ray source, which is configured for focusing said X-ray beam and is moreover associated in a vacuum-tight way to said first vacuum chamber.

In variant embodiments, the above apparatus comprises a thermal shield between said first and second vacuum chambers and said product sample, comprising a window at said output of the apparatus. In particular, it includes a housing comprising at least one bottom portion configured for operating as thermal shield, which is in particular made of ceramic material.

In variant embodiments, the apparatus comprises a mechanical arrangement configured for modifying an angle between an axis of said X-ray beam and an axis of observation of the detector in order to modify a position, in particular the depth and/or the horizontal position, of a focus of the X-ray beam.

In variant embodiments, the mechanical arrangement comprises a mechanical sub-arrangement for varying an angle of incidence calculated between the axis of the beam and an axis perpendicular to the surface of the sample, and a further mechanical sub-arrangement for displacing the axis of observation to an angle of observation with respect to the perpendicular axis in an independent way.

In variant embodiments, the apparatus comprises a module for measuring the height of the surface of the product sample, in particular an optical interferometer.

The solution described herein also relates to a method for selecting products on the basis of their composition via X-ray fluorescence spectroscopy that uses an apparatus as described above.

In variant embodiments the method envisages:

setting said selection apparatus in one or more control points of a line for producing or conveying products;

given types of product being processed in a given time interval, defining a set of significant chemical elements designed to recognise said types of product being processed; and acquiring via X-ray fluorescence spectroscopy a measurement signal of a sample of said product travelling along said production or conveying line and analysing it limitedly to said set of significant chemical elements.

In variant embodiments, the method envisages that said products are metal-matrix products and said line is a steel-production line.

In variant embodiments, the method envisages modifying an angle between an axis of said X-ray beam and an axis of observation of the detector for varying a depth of the focus of the X-ray beam, in particular as a function of the height measured by said module for measuring the height of the surface of the product sample, said module being in particular an optical interferometer.

BRIEF DESCRIPTION OF THE DRAWINGS

Various embodiments will now be described, purely by way of example, with reference to the annexed drawings, wherein:

FIGS. 2a-2d shows a diagram of axes and movements of the apparatus described herein;

FIG. 4 is a schematic perspective view of the apparatus described herein; and

FIG. 5 is a schematic illustration of a context of application of the apparatus described herein.

DETAILED DESCRIPTION

In the ensuing description numerous specific details are provided in order to enable maximum understanding of the embodiments provided by way of example. The embodiments may be implemented with or without specific details, or else with other methods, components, materials, etc. In other circumstances, well-known structures, materials, or operations are not illustrated or described in detail so that aspects of the embodiments will not be obscured. Reference in the course of this description to "an embodiment" or "one embodiment" means that a particular peculiarity, structure, or characteristic described in connection with the embodiment is comprised in at least one embodiment. Hence, phrases such as "in an embodiment" or "in one embodiment" that may appear in various points in the course of the present description do not necessarily refer to one and the same embodiment. Moreover, the particular peculiarities, structures, or characteristics may be combined in any convenient way in one or more embodiments.

The references are provided herein only for convenience of the reader and do not define the scope or the meaning of the embodiments.

Figure 1:
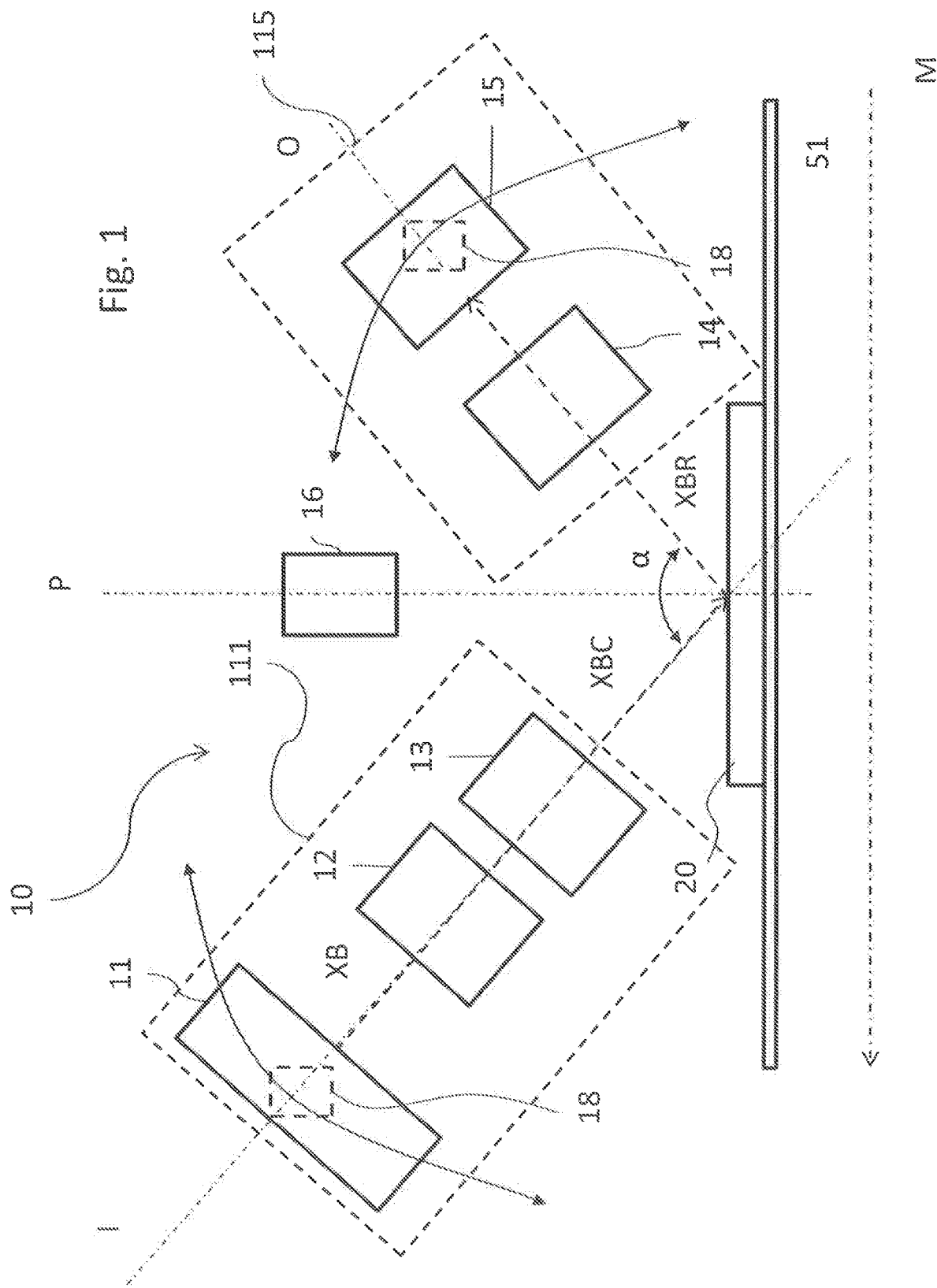
FIG. 1 shows the apparatus described herein.

FIG. 1 is a schematic illustration of an apparatus 10 for selecting products on the basis of their composition via X-ray fluorescence spectroscopy. The aforesaid apparatus 10 comprises an X-ray source, in particular an X-ray tube 11, which emits an X-ray beam XB along an axis of the beam, which corresponds to an axis of incidence I, towards a product sample 20, specifically a steel bar carried by a conveyor belt 51 in a conveying direction M. Downstream of the X-ray tube 11, the X-ray beam XB passes through an optical module 12 with polycapillary lens, substantially comprising a polycapillary lens, the principal axis of which is aligned to the axis of the beam XB, the module 12 being configured for focusing the X-ray beam in a focused beam XBC. The aforesaid focused beam XBC reaches the product sample 20 passing through a vacuum chamber 13 and is reflected, more specifically diffused, in a reflected X-ray beam XBR, along an axis of observation O. The aforesaid reflected X-ray beam passes through a further vacuum chamber 14, set on the axis of observation O and is collected and measured by an energy-dispersion solid-state particle detector 15, the axis of observation O of which, in the example, is aligned to the axis of observation O. The vacuum chambers 13 and 14 give out onto the product sample 20 via respective beryllium windows, not illustrated in FIG. 1, which close an output terminal portion 13a of the chamber 13 and an input terminal portion 14a of the chamber 14 that face the product sample 20.

Basically, the source 11, the optical module with polycapillary lens 12 and the vacuum chamber 13 identify a source assembly 111, whereas the vacuum chamber 14 and the detector 15 identify a detector assembly 115. The portion 13a substantially corresponds to the output for the focused beam XBC towards the sample 20, which, as illustrated in FIG. 4, in turn corresponds to a window 45 of the bottom 44 of a housing 43 that houses the components represented schematically in FIG. 1.

The apparatus 10 further comprises a system 18 for varying an angle α between the source and the detector, the system being configured for rotating the axis of incidence I and the axis of observation O, substantially about a respective axis of rotation of the source and of the detector, perpendicular to the plane of the drawing (direction Y, as described more fully in what follows) and passing through the terminal portion 13a and 14a, respectively, so as to vary the aforesaid source-detector angle α. As discussed also hereinafter with reference to FIGS. 2a-2d, the terminal portions 13a and 14a are preferably fixed in an rotatable way, in particular on pins 13b, 14b rotating about the aforesaid axes of rotation of the source 11 and of the detector 15, whereas the rest of the assemblies 111 and 114, basically in the median or distal part thereof with respect to the portions 13a, 14a, are constrained to move along an arc of a circle (for example, the guides 33, 34 illustrated in FIG. 3).

By varying the source-detector angle α, it is possible to modify a depth d of the position of a measurement focus F so as to excite the atoms present on the sample 20 that is to be analysed, even in the case where these are located underneath below an undesirable surface layer of material (for example, a layer of oil or oxide, which may present a variable thickness of the order of tenths of a millimetre) without modifying the tool-to-target distance and guaranteeing the possibility of always making contactless measurements.

The interferometer 16, an axis of measurement of which, perpendicular to the plane of the product sample 20, is designated by P, is used for measuring the height of the profile of the surface of the product sample 20. Via the combined use of the information on the profile of the surface of the product sample 20 of the aforesaid interferometer 16 and via the system 18 for varying an angle between the source 11 and the detector 15, it is possible to vary the source-detector angle α according to the defectiveness of the sample, understood as surface undulation, which may vary in the course of the measurement with the product moving.

As has been mentioned, the product sample 20, i.e., in the example regarding a steel-production line, the steel bar, is usually at a high temperature (up to 1200° C.) and is moreover moving. For these two reasons, it is necessary to be able to make the XRF measurement in short times, and in particular to move the X-ray source 11 and the detector 15 away from the product 20 in order to prevent them getting damaged by the heat. However, by so doing, the efficiency, precision, and speed of measurement deteriorate.

The apparatus 10 described herein exploits the presence of the vacuum chambers 13 and 14 and of the optical module 12 with polycapillary lens to follow the product 20 along the axis of movement M.

The apparatus 10 moreover exploits the presence of vacuum chambers 13 and 14 and of the optical module 12 with polycapillary lens, as well as additionally of a thermal shield described more fully hereinafter, for shielding the source 11 and the detector 15 from the high level of heat of the product 20.

This as a whole enables reduction by a factor greater than or equal to 10 of the measurement time required for the XRF analysis, without forgoing a good resolution, keeping the X-ray source and the detector at a safety distance from the product under examination.

The use of a vacuum system, represented by the vacuum chambers 13 and 14, in addition to acting as thermal insulation, enables improvement of the optical path of the X-ray beam, in particular of the focused beam XBC and of the reflected beam XBR. In particular, the intensity of the focused X-ray beam XBC does not undergo any attenuation, apart from the passage through the beryllium window and the attenuation due to the residual distance in air (for example, 1.5 cm as against approximately 10 cm in a conventional system). Consequently, the attenuation of the beam is drastically reduced, thus enabling recognition of elements such as Si, P, S (in the so-called sulphur marks), which, with the prior-art techniques, yielded a signal that was too weak to be detected, or else such as V, Cr, Mn, Fe, and possibly also Co, Ni, Cu, which yielded a weak signal (e.g., with a transmittance below 90%) and hence required longer measurement times to acquire a significant measurement signal, times that are not compatible with the high temperature of the sample being measured.

The use of the optical module 12 with polycapillary lenses moreover enables focusing on the target, i.e., of the product 20, of the X-rays produced, thus obtaining a larger number of fluorescence X-rays and reducing the time of exposure necessary to perform the required chemical analysis. The ratio between the intensity of the X-ray beam that reaches the sample 20 with the optical module 12 with polycapillary lens and without the optical module 12 with polycapillary lens is greater than 10:1, i.e., greater by one order of magnitude. The measurement time is reduced accordingly by one order of magnitude or more.

Even though in FIG. 1 the vacuum chamber 13 is represented as a block set downstream of the optical module 12 with polycapillary lens, in effect the optical module 12 with polycapillary lens is contained within the vacuum chamber 13, albeit in the part furthest from the terminal portion 13. This means that the entire path of the X-ray beam is in a vacuum, without the intensity thereof being jeopardized by stretches in air. Moreover this prevents the environmental conditions present in the production site, in the case in point a steel-production site, which involves high temperatures, dirt, and humidity, from damaging the aforesaid optical module 12 with polycapillary lens, which, in the configuration proposed herein, is protected by the presence of the vacuum itself.

The same applies to the detector 15 that is contained in the vacuum chamber 14.

Figure 2C:
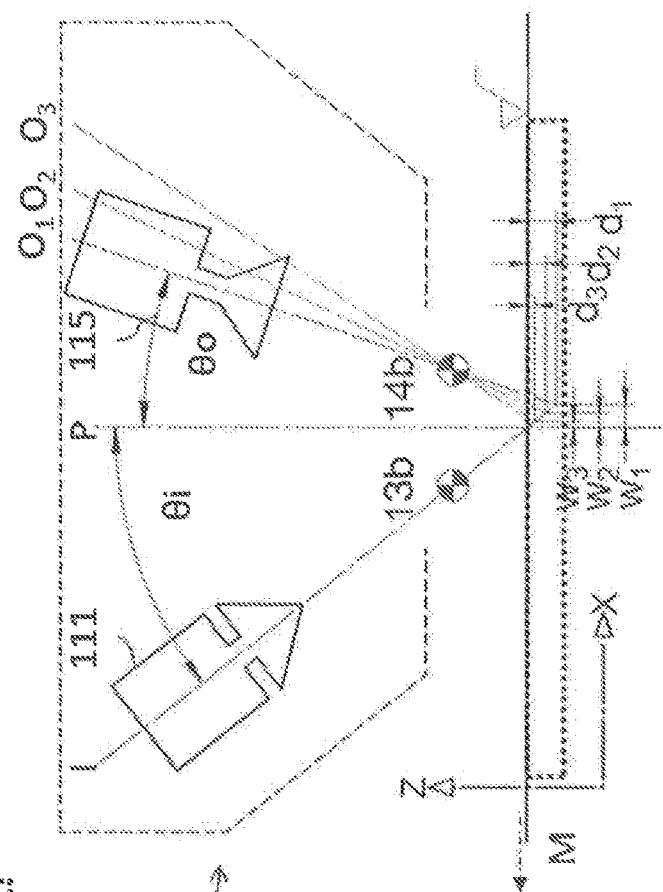
Figure 3:
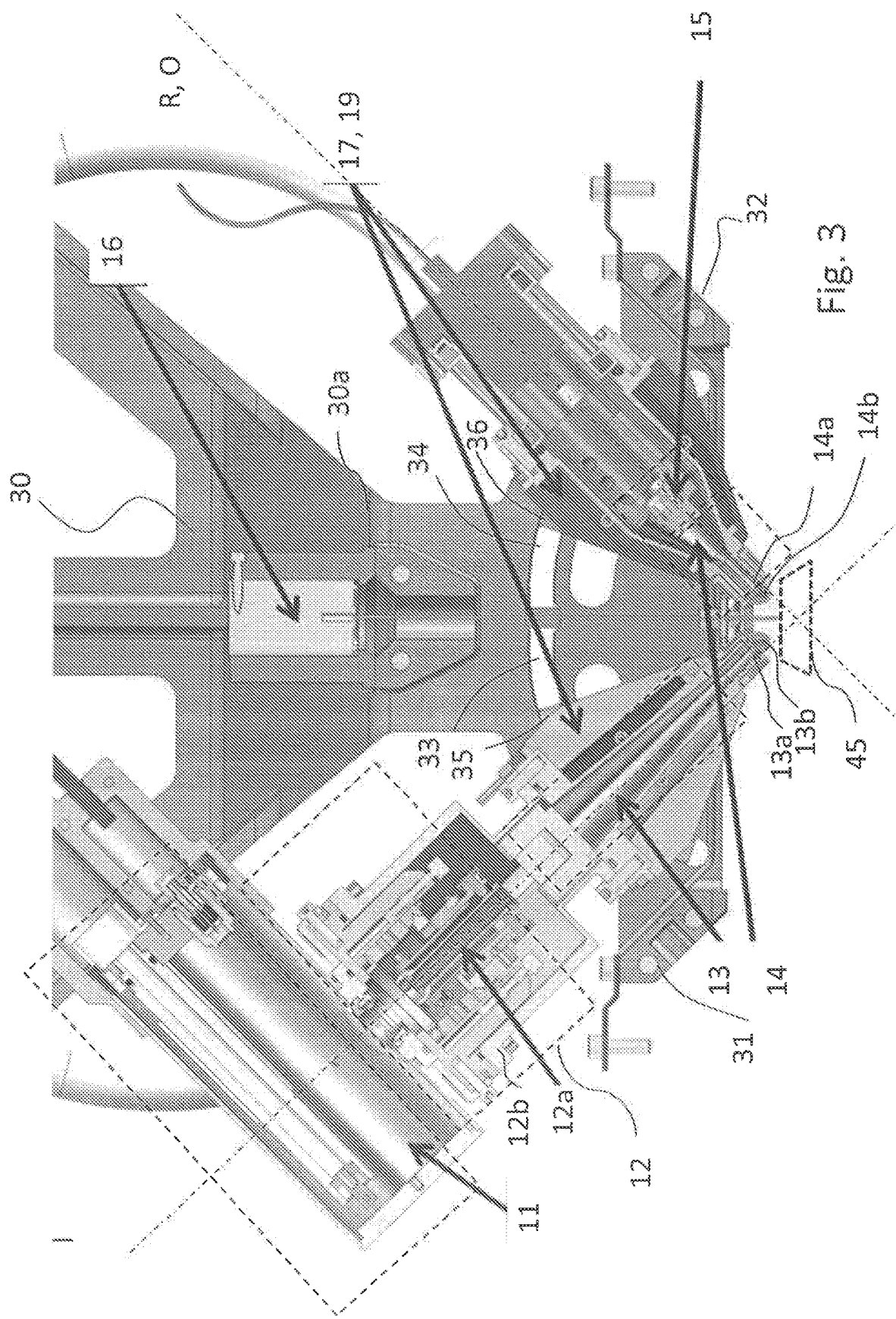
FIG. 3 is a cross-sectional view of a part of an implementation of the apparatus described herein.

Represented in FIG. 2a is a diagram that shows schematically a first mode of movement of the apparatus described, the apparatus 10 being illustrated in greater detail in FIG. 3.

As is also illustrated in what follows with reference to FIG. 3, terminal portions 13a and 14a are preferably fixed in an rotatable way on rotating articulation pins 13b, 14b, which turn about the aforesaid axes of rotation of the source 11 and of the detector 15, whereas the rest of the assemblies 111 and 114, basically in the median or distal part thereof with respect to the portions 13a, 14a, are constrained to move along an arc of a circle (for example, the guides 33, 34 illustrated in FIG. 3).

In FIG. 2a, where the horizontal axis X, parallel to the axis of movement M, and the vertical axis Z are represented (the axis Y exits from the plane of the sheet and is not represented), it may be noted how the aforesaid articulation pins 13b, 14b, and hence the terminals 13a, 14a, are located at a short distance, for example of approximately one centimetre, above the surface of the sample 20.

In this first mode, the source 11, i.e., the source assembly 111, is displaceable in such a way that the axis of incidence I of the X-ray beam XB varies an angle of incidence θi thereof, calculated between the axis of incidence I and the perpendicular measurement axis P, rotating about the articulation pin 13a. In the same way, the detector 15 can be displaced so as to align its own axis of observation O to an angle of observation θo in order to follow the consequent variation of inclination of the angle of reflection, and hence of an axis of reflection R, of the beams. In the first mode described with reference to FIGS. 2a and 2b, it is hence envisaged to vary the angle of incidence θi and the angle of observation θo, the sum of which determines the source-detector angle α, in a symmetrical way, i.e., getting them to assume equal values. In this way, a focus F varies its own position along the axis Z, changing the depth d of the focus F, in the sample 20, but its horizontal co-ordinate continues to correspond with the measurement axis P. Preferably, via the mechanical arrangement of the guides 33, 34 illustrated in FIG. 3, the optical module 12 with polycapillary lens and the vacuum chamber 13, when the source-detector angle α varies, rotate with the source 11, maintaining the alignment along the axis of incidence I, and the same applies to the chamber 14 and the detector 15.

Figure 2D:
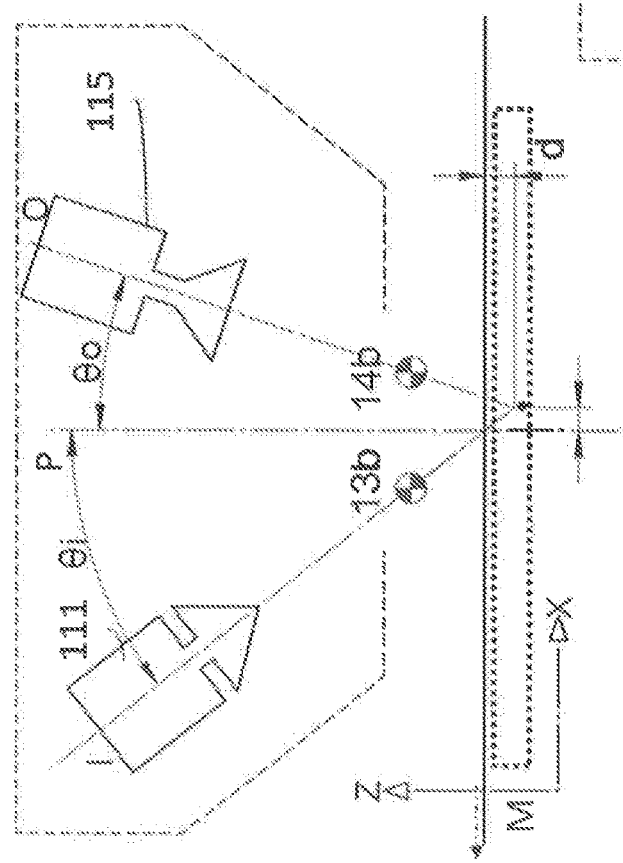

With reference to FIGS. 2c and 2d a second mode is illustrated, in which the angle of incidence θi varies with respect to the angle of observation θo in an independent way.

As illustrated in FIG. 2c, this means that the focus F is located at a depth d, but displaced by a length W with respect to the position of the axis of measurement P when the angles are symmetrical, as in FIG. 2b.

In this way, for example, as illustrated in FIG. 2d, it is possible to displace and incline in a different way the axis of observation (represented by the axes $O_1$, $O_2$, $O_3$), to obtain three different positions ($w_1$, $d_1$) ($w_2$, $d_2$) ($w_3$, $d_3$). As illustrated in FIG. 2b, by varying the source-detector angle α, which is sum of the angle of incidence θi and angle of observation θo, if the focused X-ray beam XBC is focused in the focus F, the depth d of the aforesaid focus F can be varied. The source-detector angle α is preferably referred to rotation with respect to the intersection of the axis of incidence I with the axis P of FIG. 2.

FIG. 3 illustrates, in cross-sectional view in a plane substantially defined by the axis of incidence I and the axis of reflection R, an implementation of the apparatus 10 for selecting products on the basis of their composition via X-ray fluorescence spectroscopy. As may be noted, a frame 30 is provided that has a central body 30a, which in the bottom part comprises a horizontal bracket 31 that projects outwards from the body 30a and supports the vacuum chamber 13. The aforesaid vacuum chamber 13 substantially has the shape of a conical nozzle, kept in vacuum conditions, the tapered output part of which, i.e., the terminal portion 13a, gives out onto the sample 20 (not illustrated in the figures) and is in turn contained within a chamber 17 of ceramic material for further thermal insulation. A horizontal bracket 32 moreover projects outwards from the bottom part of the body 30a in a direction opposite to the direction of projection of the bracket 31 and supports the vacuum chamber 14, which is also shaped like a conical nozzle with tapered output part, i.e., the terminal portion 14a, giving out onto the sample 20 and is contained in a corresponding chamber 19 of ceramic material, as well as the detector 15.

Provided on the horizontal brackets 31 and 32 are respective guides 33 and 34 shaped like an arc of a curve. The vacuum chambers 13 and 14 are associated to the guides via slides 35 and 36, fixed in their top or distal part with respect to the portions 13a, 14a. The portions 13a and 14a are, instead, fixed to the frame 30 so as to be able to rotate about perpendicular axes passing through the aforesaid portions 13a, 14a. Motor-driven actuators, not illustrated in FIG. 1, move the chambers 13 and 14, i.e., the assemblies 111 and 115, along the guides 33 and 34, whereas the ends 13a, 14a remain fixed, thus causing variation of the inclination of the axes I and O with respect to the aforesaid points of articulation represented by the portions 13a and 14a.

Hence, basically, the mechanical components 33, 34, 35, 36 13b, 14b identify a mechanical arrangement, or mechanical system, configured for modifying an angle α between an axis I of the aforesaid X-ray beam XB and an axis of observation O of the detector 14 in order to modify a position, in particular a depth d and/or a horizontal position w, of a focus F of the X-ray beam XB. As has been said, this arrangement comprises a mechanical sub-arrangement identified by the mechanical components 33, 34, 13b for varying an angle of incidence θi calculated between the axis I of the beam XB and an axis P perpendicular to the surface of the sample 20, i.e., the measurement axis, and a further mechanical sub-arrangement identified by the mechanical components 35, 36, 14b for displacing the axis of observation O to an angle of observation θo with respect to the perpendicular axis P in an independent way, so as to be able to vary also the horizontal co-ordinate w of the focus F.

FIG. 3 also illustrates how the optical module 12 with polycapillary lens comprises a polycapillary lens 12a and an orientation support 12b associated to the source 11 so that it can translate and rotate along a plurality of axes in order to align the polycapillary lens 12a correctly.

FIG. 4 illustrates, instead, a housing 44 of the apparatus 10, which contains within it the frame 30 with all the components of the apparatus 10 represented in FIG. 3 (or represented schematically in FIG. 1). The aforesaid housing 43, substantially shaped like a tank or basket, has a bottom part 44, facing the product sample 20 and provided with an output window 45, through which there can pass the focused X-ray beam XBC at output from the apparatus 10 and the reflected X-ray beam XFR, as well as the beam of the optical interferometer 16. In this regard, represented in FIG. 4 are the respective axes of incidence I, reflection R, and interferometric measurement P, which exit from the aforesaid output window 45. Since the aforesaid bottom part 44 faces the product sample 20, it is configured as thermal shield, in particular made of ceramic material of the type used as thermal shield in the aerospace industry, for example, ceramic silica. The window 45 is represented dashed also in FIG. 3, to facilitate understanding even though the housing 43 is not represented therein.

The housing 43 moreover has, in its top part, bars 46 and 47 for fixing it to a positioning system, for example, a robot manipulator 52, as discussed with reference to FIG. 4.

Moreover designated by 49 is a pneumatic safety shutter. The aforesaid shutter 49 rotates for closing the window 45 so as to prevent passage of the beam XBC except when the measurement is made. In other words, the shutter 49, illustrated open in FIG. 4 for carrying out the measurement, is normally closed. The shutter 49 comprises in a portion 49a thereof for closing the window 45 a plate of a known chemical composition, for example steel of a known mark, for calibrating the apparatus 10.

Hence, in general with reference to FIGS. 1 to 4, an apparatus 10 for selecting products on the basis of their composition via X-ray fluorescence spectroscopy has been described, which comprises an X-ray source 11 that emits an X-ray beam XB towards a product sample 20, and a particle detector 15 for receiving an X-ray beam XBR diffused by said product sample 20 and generating a signal received that can be analysed to determine a chemical composition of said product sample 20 and select a type of product corresponding to said chemical composition of the product sample 20, said apparatus 10 comprising a first vacuum chamber 13 located between an output, the window 45, of the apparatus 10 facing the product sample 20 and said X-ray source 11, and a second vacuum chamber 14 located between said output 45 of the apparatus 10 facing the product sample 20 and said detector 15, where the apparatus 10 also comprises an optical module 12 with polycapillary lens located downstream of said X-ray source 11, configured for focusing said X-ray beam XB and moreover associated in a vacuum-tight way to said first vacuum chamber 13, in particular upstream of said first vacuum chamber 13.

FIG. 5 represents schematically a context of use of the product-selection apparatus 10 described herein.

The aforesaid apparatus 10 operates under the control of a control module 60, which is configured for controlling operation of the XRF system, i.e., in particular of the source 11, of the detector 15, of the interferometer 16, and of the system 18 for varying the angle.

The aforesaid control module 60 comprises a software analysis module 61 that receives an XRF measurement signal Y of the apparatus 10, i.e., of the detector 15, and analyses it to determine a chemical composition of the product sample 20 travelling along the production line, which in the figures is designated by the reference 50 and comprises, inter alia, the conveyor 51 on which the apparatus 10 operates.

The aforesaid software analysis module 61 receives as input a list LS of significant chemical elements for recognising the products being processed on the production line 50, for example referred to a given time interval, for instance within one day, one week, or one month. The aforesaid list LS relates in general to a reduced set as compared to the set of chemical elements that can be identified by the apparatus 10.

The software analysis module 61 is connected in an access relationship to a database CDB, stored in the records of which are at least the reference chemical compositions corresponding to the various types of product being processed in the time interval or that can be processed on the production line, or else to the casting composition.

The software analysis module 61, on the basis of the measurement signal Y, the list LS, and the data contained in the database CBD, identifies the type of product C and supplies it to a decider module 62, which on the basis thereof, issues a command to the production line 50 to perform an action. For instance, if the product 20 passing is of an unexpected type C, it can issue commands to branching points downstream of the control point in which the apparatus 10 operates in order to convey the unexpected product 20 towards the reject line, so as to prevent mixing of products 20 of a different type, in particular of steel bars of a different mark.

It should be noted that the control module 60 also receives a synchronisation signal T from the production line, i.e., for example a signal that supplies the time scan at which the samples present on the conveyor 51 so as to be able to synchronise the measurement operations.

The control module 60, in this regard, is also configured for controlling a robot manipulator 52, which moves the apparatus 10, for example along the conveyor 51, according to the requirements of measurement and operation of the production line.

The control module 60 is moreover connected, through a network 70, which may be the Internet or a mobile-telephone network or a communication network of some other type, to terminals 80, personal computers, and/or smartphones, and/or tablets, with are equipped with applications for communicating with the control module 60 both for displaying data and for sending commands.

The software analysis module 61 is in general configured for carrying out the following functions on the measured signal Y:
acquisition;
correction;
smoothing;
removal of noise;
detection of peaks of the spectrum obtained from the measured signal Y;
operations of non-linear fitting of the data of the spectrum;
integration of the peaks;
calculation, from the value of the peak integral, of concentrations of chemical elements for determining the chemical composition of the sample measured; and
comparison of measured chemical compositions c with compositions stored in the database DCB, in particular for recognising the type C of product.

Not necessarily can all the operations, in variant embodiments of the solution described herein, be present in the analysis; for example, one or more of the operations of correction, smoothing, and removal of noise may not be present, but a possible embodiment comprises the operations referred to above in the order in which they are presented.

Hence, the apparatus 10 described for selecting products on the basis of their composition via X-ray fluorescence spectroscopy in a production line 50 may be installed along the various processing lines, for example before each branching, at input and/or at the end of each different processing line.

As mentioned previously, the apparatus 10 must be able to perform the chemical analysis and recognition of moving targets, at speeds that may reach 80 m/min. It is thus necessary to complete the measurement in a short time.

For this purpose it is envisaged to supply, prior to the measurement made by the apparatus 10, the indication of what are the significant chemical elements for discriminating the different types C, or marks, of product 20 being processed, i.e., the list LS. This makes it possible to establish in shorter times recognition of the type of product 20 being processed and hence prevent problems of mixing between the different types of product 20, in the example described herein mixing between different long metal-matrix sectional elements.

In fact, once the apparatus 10 the carries out the XRF spectroscopy measurement has made the quantitative measurement, i.e., the measurement of the values of concentration of the chemical elements present in the product 20 being measured and necessary for recognition of the type of product being processed, for example limitedly to the ones indicated in the list LS, it is sufficient to compare the results of the aforesaid analysis with the data of a reference chemical composition, for example the casting chemical composition or the chemical composition of the type of product, i.e., of the mark, stored in the database CDB in order to recognise the type of product 20 and prevent mixing between the different products, for example long metal-matrix sectional elements.

Since the aforesaid comparison, which in general may envisage verification of the concentrations of all or a large number of chemical elements, is preferably made via measurement with respect to the list LS of significant chemical elements, which is a reduced set, is much faster and enables limitation of the measurement time, and hence exposure of the apparatus 10 to high temperatures.

With the apparatus 10 described, it is possible to carry out control, for example via the module 60 that controls the line 50, in any point of the production line, for example at the start or at the end of a new processing operation, in the presence of a junction. In general, there are in any case no limits to the number of control points that can be used on the lines.

Hence, in a general form, the solution described herein is aimed at a method for selecting products on the basis of their composition via X-ray fluorescence spectroscopy that uses an apparatus like the apparatus described herein, which envisages:
setting said selection apparatus in one or more control points of a line for producing or conveying products;
given types of product being processed in a given time interval, defining a set of significant chemical elements designed to recognise said types of product being processed; and
measuring a chemical composition of a sample of said product travelling along said production or conveying line limitedly to said set of significant chemical elements.

Hence, from what has been said so far, the solution described and the corresponding advantages emerge clearly.

The apparatus according to the invention advantageously makes it possible to conduct a chemical analysis on samples of product in a continuous production flow.

The apparatus described, thanks to introduction of the vacuum chamber and of the module with polycapillary lens, solves the problem of intense heat thanks both to the thermal insulation and to the shorter acquisition time.

The aforesaid components also enable optical improvements in following the product along the axis of movement.

This as a whole enables considerable reduction of the times of analysis without forgoing a good resolution, maintaining the X-ray source and the detector at a safety distance from the product under examination.

Advantageously, the vacuum chambers also prevent the environmental conditions present in the production site, in the case in point a steel-production site, which involve high temperatures, dirt, and humidity, from damaging the optical modules, but also the source or the detector.

Of course, without prejudice to the principle of the invention, the details and embodiments may vary, even significantly, with respect to what has been described herein purely by way of example, without departing from the sphere of protection. The aforesaid sphere of protection is defined by the annexed claims.

The apparatus and method described and claimed herein are preferably applied to the selection of metal-matrix products, for example steel sectional elements, which travel on the lines at high temperatures.

However, the apparatus and method described herein apply also to products that are not necessarily metal products, but the composition of which can be analysed via XRF spectroscopy. In addition, of course, it is possible to examine also products at temperatures such as not to cause damage to the apparatus.

The invention claimed is:

1. An apparatus for selecting products on the basis of their composition via X-ray fluorescence spectroscopy, comprising an X-ray source that emits an X-ray beam towards a product sample, and a particle detector for receiving an X-ray beam diffused by said product sample and generating a received signal suitable to be analysed to determine a chemical composition of said product sample and select a type of product corresponding to said chemical composition of the product sample,
    wherein said apparatus comprises
    a bottom portion facing said product sample comprising an output window facing the product sample, an axis of said X-ray beam and an observation axis of the detector passing through said output window,
    a first vacuum chamber located between said output window of the apparatus facing the product sample and said X-ray source on said axis of said X-ray beam, and a second vacuum chamber located between said output window of the apparatus facing the product sample and said detector on said observation axis of the detector,
    a system of variation of angle (a) between the axis of said X-ray beam of said X-ray source and the observation axis of said detector, said system being configured to rotate the axis of said X-ray beam and the observation axis about respective axes of rotation perpendicular to a plane they lie within.

2. The apparatus according to claim 1, wherein said apparatus further comprises an optical module with polycapillary lens located downstream of said X-ray source, which is configured for focusing said X-ray beam and is moreover associated in a vacuum-tight way to said first vacuum chamber.

3. The apparatus according to claim 2, wherein it comprises a housing, which includes said bottom portion configured for operating as thermal shield, corresponding to said bottom portion facing said product sample comprising an output window facing the product sample.

4. The apparatus according to claim 1 said apparatus for selecting products on the basis of their composition via X-ray fluorescence spectroscopy comprises a thermal shield between said first and second vacuum chambers and said product sample, said thermal shield comprising said output window at said bottom portion of the apparatus.

5. The apparatus according to claim 1, wherein the system of variation of angle comprises a mechanical arrangement configured for modifying an angle between the axis of said X-ray beam and the observation axis of the detector in order to modify a position of a focus of the X-ray beam.

6. The apparatus according to claim 5, wherein said mechanical arrangement comprises a mechanical sub-arrangement for varying an angle of incidence calculated between the axis of the beam and an axis perpendicular to the surface of the product sample, and a further mechanical sub-arrangement for displacing the observation axis to an angle of observation with respect to the perpendicular axis in an independent way.

7. The apparatus according to claim 5, wherein said position is a depth and/or a horizontal position, of the focus of the X-ray beam.

8. The apparatus according to claim 1, wherein it comprises a module for measuring the height of a profile of the surface of the product sample.

9. A method for selecting products on the basis of their composition via X-ray fluorescence spectroscopy that uses an apparatus for selecting products on the basis of their composition via X-ray fluorescence spectroscopy, comprising
    emitting an X-ray beam from an X-ray source towards a product sample, and
    receiving at a particle detector an X-ray beam diffused by said product sample and
    generating a received signal suitable to be analysed to determine a chemical composition of said product sample and
    selecting a type of product corresponding to said chemical composition of the product sample,
    wherein
    a bottom portion of said apparatus facing said product sample comprises an output window facing the product sample, an axis of said X-ray beam and an observation axis of the detector passing through said output window,
    it comprises a first vacuum chamber located between said output window of the apparatus facing the product sample and said X-ray source on said axis of said X-ray beam, and a second vacuum chamber located between said output window of the apparatus facing the product sample and said detector on said observation axis of the detector,
    comprising rotating said axis of said X-ray beam and said observation axis about respective axes of rotation perpendicular to the plane they lie within by a system of variation of angle (a) between the axis of said X-ray beam of said X-ray source and the observation axis of said detector, comprised in said apparatus.

10. The method according to claim 9, further including:
    setting said apparatus for selecting products in one or more control points of a line for producing or conveying products;
    given types of product being processed in a given time interval, defining a set of significant chemical elements designed to recognise said types of product being processed; and
    acquiring via X-ray fluorescence spectroscopy a measurement signal of a sample of a product travelling along said production or conveying line and analysing it limitedly to said set of significant chemical elements.

11. The method according to claim 10, wherein said products are metal-matrix products and said line for producing or conveying products is a steel-production line.

12. The method according to claim 9, wherein it comprises modifying an angle between said axis of said X-ray beam and said observation axis of the detector for varying and/or modifying a position of a focus of the X-ray beam.

13. The method according to claim 12, wherein said position is a depth and/or a horizontal position of a focus of the X-ray beam, and includes varying and/or modifying said position as a function of a height measured by a module for measuring the a profile of the surface of the product sample, said module being an optical interferometer.

* * * * *